(12) United States Patent
Lee et al.

(10) Patent No.: US 8,101,138 B2
(45) Date of Patent: Jan. 24, 2012

(54) CENTRIFUGAL MAGNETIC POSITION CONTROL DEVICE, DISK-SHAPED MICRO FLUIDIC SYSTEM INCLUDING THE SAME, AND METHOD OF OPERATING THE COMPACT DISK-SHAPED MICRO FLUIDIC SYSTEM

(75) Inventors: Jeong-gun Lee, Yongin-si (KR); Yoon-kyoung Cho, Yongin-si (KR); Beom-seok Lee, Yongin-si (KR); Jong-myeon Park, Yongin-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 993 days.

(21) Appl. No.: 11/837,038

(22) Filed: Aug. 10, 2007

(65) Prior Publication Data

US 2008/0035579 A1    Feb. 14, 2008

(30) Foreign Application Priority Data

Aug. 11, 2006  (KR) .................. 10-2006-0076369
Jan. 3, 2007   (KR) .................. 10-2007-0000703

(51) Int. Cl.
*B01L 3/00*     (2006.01)
*F04B 19/00*    (2006.01)

(52) U.S. Cl. .......... 422/506; 422/72; 436/177; 210/787; 210/512.1; 210/223; 210/695; 210/380.3; 494/85; 494/42; 494/84; 494/66

(58) Field of Classification Search .......... 422/72, 422/502, 506, 50, 101, 102, 68.1, 504, 527, 422/533, 537, 554; 210/222, 223, 695, 787, 210/800–802, 360.1, 380.1, 380.3, 383; 435/287.1, 435/287.3, 288.4, 288.5; 436/177; 494/84, 494/42, 36, 44, 56, 85, 66; 366/273–274
See application file for complete search history.

(56) References Cited

U.S. PATENT DOCUMENTS

| | | | | |
|---|---|---|---|---|
| 1,603,175 A | * | 10/1926 | Weisz | 15/220.2 |
| 5,061,381 A | * | 10/1991 | Burd | 210/789 |
| 5,173,193 A | * | 12/1992 | Schembri | 210/782 |
| 5,173,262 A | * | 12/1992 | Burtis et al. | 422/72 |
| 5,222,808 A | * | 6/1993 | Sugarman et al. | 366/274 |
| 5,242,803 A | * | 9/1993 | Burtis et al. | 435/7.92 |

(Continued)

OTHER PUBLICATIONS

Communication (Extended European Search Report) issued on Feb. 3, 2011, in counterpart European Patent Application No. 07104742.7.

*Primary Examiner* — Tony G Soohoo
*Assistant Examiner* — David C Mellon
(74) *Attorney, Agent, or Firm* — Sughrue Mion, PLLC (57) ABSTRACT

A centrifugal micro fluidic system and a centrifugal magnetic position control device used in the centrifugal micro fluidic system for controlling the position of magnetic beads are provided. The centrifugal micro fluidic system comprising, a rotatable platform; a micro fluidic structure which is disposed in the platform; and a plurality of objects which include functional groups on surfaces thereof so as to capture a target material from the fluid and carry the target material while being suspended in and separated from the fluid in the micro fluidic structure, wherein the movements of the objects are controlled by a force affecting the objects differently compared to the force's effect on the fluid. When the objects are made of a magnetic material, the force may be a magnetic force applied by the centrifugal magnetic position control device.

23 Claims, 8 Drawing Sheets

U.S. PATENT DOCUMENTS

| | | | |
|---|---|---|---|
| 5,925,573 A * | 7/1999 | Colin et al. | 436/525 |
| 5,993,665 A * | 11/1999 | Terstappen et al. | 210/695 |
| 6,037,167 A * | 3/2000 | Adelman et al. | 435/285.1 |
| 6,143,248 A * | 11/2000 | Kellogg et al. | 422/72 |
| 6,415,821 B2 * | 7/2002 | Kamholz et al. | 137/827 |
| 6,709,869 B2 * | 3/2004 | Mian et al. | 436/45 |
| 6,739,576 B2 * | 5/2004 | O'Connor et al. | 251/129.14 |
| 7,320,776 B2 * | 1/2008 | Hsieh et al. | 422/72 |
| 2004/0023273 A1 * | 2/2004 | Puget et al. | 435/6 |
| 2006/0024732 A1 * | 2/2006 | Huang et al. | 435/6 |
| 2007/0199901 A1 * | 8/2007 | Campagnolo et al. | 210/695 |

* cited by examiner

CENTRIFUGAL MAGNETIC POSITION CONTROL DEVICE, DISK-SHAPED MICRO FLUIDIC SYSTEM INCLUDING THE SAME, AND METHOD OF OPERATING THE COMPACT DISK-SHAPED MICRO FLUIDIC SYSTEM

CROSS-REFERENCE TO RELATED PATENT APPLICATION

This application claims priority from Korean Patent Application Nos. 10-2006-0076369, filed on Aug. 11, 2006 and 10-2007-0000703, filed on Jan. 3, 2007, in the Korean Intellectual Property Office, the disclosure of which are incorporated herein in their entirety by reference.

BACKGROUND OF THE INVENTION

1. Field of the Invention

Devices, systems and methods consistent with the present invention relate to a centrifugal micro fluidic system, a method of operating the centrifugal micro fluidic system, and a centrifugal magnetic position control device used in the centrifugal micro fluidic system for controlling the position of magnetic beads, and more particularly, to a centrifugal magnetic position control device capable of controlling the position of a magnet disposed in a micro fluidic structure using centrifugal and magnetic forces by placing another magnet in a neighboring layer to the micro fluidic structure so as to control the position of magnetic beads in the micro fluidic structure formed in a layer of a disk-shaped platform, a centrifugal micro fluidic system including the centrifugal magnetic position control device, and a method of operating the centrifugal micro fluidic system.

2. Description of the Related Art

A target biomaterial is separated from a biological sample, such as blood plasma, via methods using silica, glass fiber, anion-exchange resin, or magnetic beads. In the method using magnetic beads, magnetic beads having surface functional groups capable of being combined with a target biomaterial are placed in a sample to trap the target biomaterial, and are then separated from the sample in order to extract the target biomaterial from the magnetic beads. Thus, the magnetic beads separation method has been widely used in order to separate cells, proteins, nucleic acids, or other bio-molecules. For example, U.S. Pat. No. 6,893,881 discloses a method of separating specific target cells using paramagnetic beads coated with antibodies.

Meanwhile, recently, a micro fluidic system that can perform various reactions in a single unit in order to analyze and process a sample solution has been proposed. As one example in this regard, a compact disk (CD)-shaped micro fluidic system which moves a solution sample using a centrifugal force in a compact disk-shaped micro fluidic unit has been developed. Then, to perform a desired task using magnetic beads in the compact disk-shaped micro fluidic system, the position of the magnetic beads should be controlled independently from the movement of the solution sample.

SUMMARY OF THE INVENTION

The present invention provides a centrifugal micro fluidic system comprising, a rotatable platform; a micro fluidic structure which is disposed in the platform and includes a chamber which is capable of accommodating a fluid, a channel through which the fluid can flow, and a valve which controls the flow of the fluid; and a plurality of objects which include functional groups on surfaces thereof so as to capture a target material from the fluid and carry the target material while being suspended in and separated from the fluid in the micro fluidic structure, wherein the movements of the objects are controlled by a force affecting the objects differently compared to the force's effect on the fluid. For example, the force may be a magnetic force when the objects are made of a magnetic material. Otherwise, the force may also be a centrifugal force or a gravitational force. The objects may be made of a variety of materials such as metal, metal oxide, semiconductor, organic material, polymer or a composition thereof. The objects may also have a variety of forms such as a bead, a flake, a strip or a piece of fiber. For example, the objects may be magnetic beads. The movements of these magnetic beads in the micro fluidic structure can be controlled by the position of a magnet disposed outside the micro fluidic structure.

The present invention provides a centrifugal magnetic position control device and a micro fluidic system including the centrifugal magnetic position control device for controlling the position of a magnet using centrifugal and magnetic forces in order to control the position of magnetic beads independently of a centrifugal movement of a fluid carrying the magnetic beads.

According to an aspect of the present invention, there is provided a centrifugal micro fluidic system including: a rotatable platform including a first layer and a second layer disposed adjacent to a top or bottom side of the first layer; a micro fluidic structure disposed in the first layer of the platform, the micro fluidic structure including a chamber capable of accommodating a fluid, a channel allowing a flow of the fluid, and a valve controlling the flow of the fluid; magnetic beads including functional groups on surfaces thereof so as to capture a target material from a sample, the magnetic beads carrying the target material while moving in the micro fluidic structure; a guide rail disposed in the second layer of the platform, the guide rail connecting a plurality of positions located along a path through which the magnetic beads move, the plurality of positions being spaced away from a rotational center of the platform at different distances; a first magnet movably disposed in the guide rail and generating a predetermined magnetic force for moving the magnetic beads; a second magnet disposed outside the platform at a location closer to the second layer than the first layer; and a driving unit rotating the platform.

The platform may be formed of a material that does not have a magnetic property nor block a magnetic force. The platform may have a disk shape. However, the platform is not limited to the disk shape. For example, the platform can be formed into a cartridge shape that can be attached to a disk, cylindrical, or conical rotary frame.

The first magnet and the second magnet may be disposed to attract each other. Alternatively, the first and second magnets may be disposed to repel each other. The position of the second magnet and rotation conditions of the platform may vary depending on whether the first and second magnets attract or repel each other. However, the second magnet may have a fixed position at least while the platform rotates regardless of whether the first and second magnets attract or repel each other. Meanwhile, the centrifugal micro fluidic system may further include a second magnet moving unit moving the second magnet in a radial direction of the platform.

The guide rail may include a section branching into two branches away from the rotational center of the platform.

The first magnet may be a permanent magnet and the second magnet may be a permanent magnet or electromagnet. The first magnet may be a magnet selected from the group consisting of a ceramic permanent magnet, a rare-earth permanent magnet, an alnico permanent magnet, and a polymer permanent magnet.

The functional groups on the surfaces of the magnetic beads may be antigens, antibodies, or metal oxides having an affinity to the target material. The metal oxides may be metal oxides selected from the group consisting of $Al_2O_3$, $TiO_2$, $Ta_2O_3$, $Fe_2O_3$, $Fe_3O_4$, and $HfO_2$. The magnetic beads may include at least one ferromagnetic material selected from the group consisting of iron (Fe), nickel (Ni), chromium (Cr), and an oxide thereof.

In an exemplary embodiment of the present invention, the micro fluidic structure may further include a trapping chamber for collecting the magnetic beads, and a reverse channel connected to the trapping chamber and extending from the trapping chamber in a direction opposite to that of a centrifugal force; and the guide rail may include a section running along the reverse channel. In this case, the magnetic beads collected in the trapping chamber may be moved in the direction opposite to that of the centrifugal force by moving the first magnet in the guide rail from a position corresponding to the trapping chamber along the section of the guide rail.

In another exemplary embodiment, the micro fluidic structure may further include a mixing chamber in which the magnetic beads are mixed with the sample, the mixing chamber including an outlet formed at a position away from the rotational center of the platform; and the guide rail may include a section running from a position corresponding to the outlet of the mixing chamber to a position corresponding to a portion of the mixing chamber, closer to the rotation center of the platform than the outlet of mixing chamber. In this case, after the magnetic beads are collected to an inside of the outlet of the mixing chamber by a centrifugal force, the magnetic beads are moved back to the portion of the mixing chamber closer to the rotation center of the platform than the outlet of the mixing chamber.

According to another aspect of the present invention, there is provided a method of operating the centrifugal micro fluidic system, the method comprising, suspending the objects in the fluid; and separating the objects from the fluid in the micro fluidic structure by applying a force affecting the objects differently compared to the force's effect on the fluid. For example, the force may be a magnetic force when the objects are made of a magnetic material. Otherwise, the force may also be a centrifugal force or a gravitational force. The objects may be made of a variety of materials such as metal, metal oxide, semiconductor, organic material, polymer or a composition thereof. The objects may also have a variety of forms such as a bead, a flake, a strip or a piece of fiber. For example, the objects may be magnetic beads. The movements of these magnetic beads in the micro fluidic structure can be controlled by the position of a magnet disposed outside the micro fluidic structure.

According to another aspect of the present invention, there is provided a method of operating the centrifugal micro fluidic system, the method including adjusting a rotational speed of the platform according to a horizontal distance between the second magnet and a position in the guide rail where the first magnet is to be placed, so as to balance a centrifugal force acting on the first magnet with a magnetic force generated between the first and second magnets.

According to another aspect of the present invention, there is provided a method of operating the centrifugal micro fluidic system in which the guide rail includes a section branching into two branches away from the rotational center of the platform. The method includes selecting a rotational direction of the platform depending on a direction of one of the two branches where the first magnet is moved; and adjusting a rotational speed of the platform according to a horizontal distance between the second magnet and a position in the guide rail where the first magnet is to be placed, so as to balance a centrifugal force acting on the first magnet with a magnetic force generated between the first and second magnets.

According to another aspect of the present invention, there is provided a centrifugal magnetic position control device, the device including: a guide rail disposed in a rotatable platform and connecting a plurality of positions spaced away from a rotational center of the platform at different distances; a first magnet movably disposed in the guide rail; a second magnet disposed outside the platform and generating a predetermined magnetic force for moving the first magnet; and a driving unit rotating the platform.

The platform may be formed of a material which does not have a magnetic property nor block a magnetic force. The platform may have a disk shape. However, the platform is not limited to the disk shape. For example, the platform can be formed into a cartridge shape that can be attached to a disk, cylindrical, or conical rotary frame.

The first magnet and the second magnet may be disposed is to attract each other. Alternatively, the first and second magnets can be disposed to repel each other. The position of the second magnet and rotation conditions of the platform may vary depending on whether the first and second magnets attract or repel each other. However, the second magnet may have a fixed position at least while the platform rotates regardless of whether the first and second magnets attract or repel each other. Meanwhile, the centrifugal magnetic position control device may further include a second magnet moving unit moving the second magnet in a radial direction of the platform.

The guide rail may include a section branching into two branches away from the rotational center of the platform.

The first magnet may be a permanent magnet and the second magnet may be a permanent magnet or electromagnet. The first magnet may be a magnet selected from the group consisting of a ceramic permanent magnet, a rare-earth permanent magnet, an alnico permanent magnet, and a polymer permanent magnet.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF EXEMPLARY EMBODIMENTS OF THE INVENTION

The present invention will now be described more fully with reference to the accompanying drawings, in which exemplary embodiments of the invention are shown.

Figure 1:
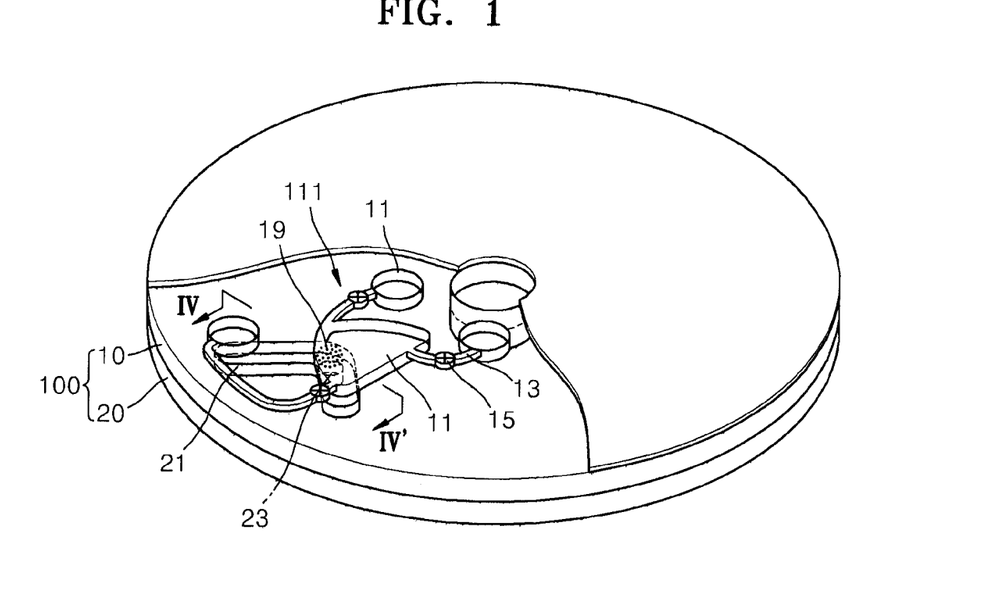
FIG. 1 is a perspective view illustrating a centrifugal micro fluidic system according to an exemplary embodiment of the present invention.

FIG. 1 is a perspective view illustrating a centrifugal micro fluidic system according to an exemplary embodiment of the present invention. A platform 100 includes first and second layers 10 and 20 that are formed integrally with each other. A micro fluidic structure 111 is formed in the first layer 10. The micro fluidic structure 111 includes chambers 11 for storing a fluid containing a test sample, channels 13 connecting the chambers 11 as fluid passages, and valves 15 for controlling flows of the fluid. The valves 15 may be passive valves that are passively opened when a predetermined condition (e.g. a pressure difference across the valve) is satisfied, such as capillary valves, hydrophobic valves or siphon valves. The valves 15 may also be active valves that are opened when power or energy is applied to the valves from the outside in response to an operating signal. The micro fluidic structure 111 accommodates magnetic beads 19. Functional groups capable of coupling with a target material contained in the fluid are fixed to the surfaces of the magnetic beads 19. After the magnetic beads 19 couple with the target material contained in the fluid, the magnetic beads 19 move in the micro fluidic structure 111 to carry the target material. Referring to FIG. 1, a capping layer covering the first layer 10 is partially removed to show the micro fluidic structure 111.

The second layer 20 includes a guide rail 21 separated from the micro fluidic structure 111 of the first layer 10. A first magnet 23 is disposed in the guide rail 21. The first magnet 23 can move freely in the first magnet 23 in a horizontal direction. The first magnet 23 forms a magnetic field such that the magnetic beads 19 can be collected close to the first magnet 23 in the micro fluidic structure 111. The second layer 20 can be disposed under the first layer 10 as shown in FIG. 1. Alternatively, the second layer 20 can be disposed above the first layer 10.

Although not shown in FIG. 1, a second magnet is disposed outside the platform 100 (specifically, under the second layer 20) to apply a magnetic force to the first magnet 23 for changing the position of the first magnet 23.

The platform 100 may be formed of a non-magnetic material that does not block a magnetic field. In this case, the first magnet 23, the second magnet (not shown), and the magnetic beads 19 can smoothly interact with one another by means of a magnetic field.

The centrifugal micro fluidic system also includes a driving unit (not shown) to rotate the platform 100 in a predetermined manner. For example, the driving unit may include a motor (not shown) having a shaft as a rotation member to rotate the platform 100, a power transmission mechanism (not shown) to transmit a driving force of the shaft to the platform 100, and a controller (not shown) to adjust the rotation speed of the platform 100 by controlling the motor. The driving unit can be easily envisioned by one of ordinary skill in the related art.

Any type of fine magnetic beads coupled with surface functional groups capable of capturing a target material can be used in the magnetic fluidic system of the present invention as the magnetic beads 19. In general, the magnetic beads 19 may have a diameter in the range of 0.001 μm to 200 μm. For example, the magnetic beads 19 can have a diameter in the range of 0.1 μm to 100 μm. The size of the magnetic beads 19 can be properly selected depending on the size of a target biomaterial to be captured and carried by the magnetic beads 19 and the inner space of the centrifugal micro fluidic system. Also, the magnetic beads 19 can be formed of any material having a magnetic property. In particular, the magnetic beads 19 can be formed of a metal, such as iron (Fe), nickel (Ni), chromium (Cr), cobalt (Co), and a metal oxide thereof having ferromagnetic property. Additionally, the magnetic beads 19 may include a material such as gadolinium (Gd), terbium (Tb), diprosium (Dy), thulium (Tm), erbium (Er), and holmium (Ho).

The kind of the surface functional groups coupled with the magnetic beads 19 can vary according to the use of the micro fluidic system. That is, the kind of the surface functional groups can be properly selected depending on the kind of a target material to be captured. The surface functional groups can be selected from one of an antigen, an antibody, and a metal oxide having an affinity for a specific material. For example, when it is intended to capture specific antigens from a biological sample such as blood, urine, or saliva, the surface functional groups may be antibodies capable of coupling with the specific antigens.

Magnetic beads coupled with antibodies capable of capturing specific cells or viruses are commercially available from Invitrogen and Qiagen companies, and commercially available magnetic beads can be used as the magnetic beads 19. For example, Dynabeads Genomic DNA Blood (Invitrogen), Dynabeads anti-*E. coli* O157 (Invitrogen), CELLection™ Biotin Binder Kit (Invitrogen), and MagAttract Virus Min M48 Kit (Qiagen) are commercially available. When such commercially available magnetic beads are used as the magnetic beads 19, Diphtheria toxin, *Enterococcus faecium, Helicobacter pylori*, HBV, HCV, HIV, Influenza A, Influenza B, *Listeria, Mycoplasma pneumoniae, Pseudomonas* sp., *Rubella virus*, and *Rotavirus* can be captured from a sample, for example.

Non-limiting examples of the metal oxide that can be used to form the magnetic beads 19 include $Al_2O_3$, $TiO_2$, $Ta_2O_3$, $Fe_2O_3$, $Fe_3O_4$, and $HfO_2$. Specifically, the metal oxide may be $Al_2O_3$ or $TiO_2$. More specifically, the metal oxide may be $Al_2O_3$. The metal oxide may be deposited on the magnetic beads 19 by a well-known method such as physical vapor deposition (PVD), atomic layer deposition (ALD), and sol-gel deposition.

The structure of the centrifugal micro fluidic system except for the first layer 10 including the micro fluidic structure 111 can be referred to as a centrifugal magnetic position control device. The centrifugal magnetic position control device of the present invention can be combined with a disk-shaped platform having a micro fluidic structure, like in the case of the micro fluidic system. Furthermore, the centrifugal magnetic position control device of the present exemplary embodiment can be combined with any apparatus requiring a magnetic field that can be varied by controlling the position of a magnet in a rotary body.

Figure 2:
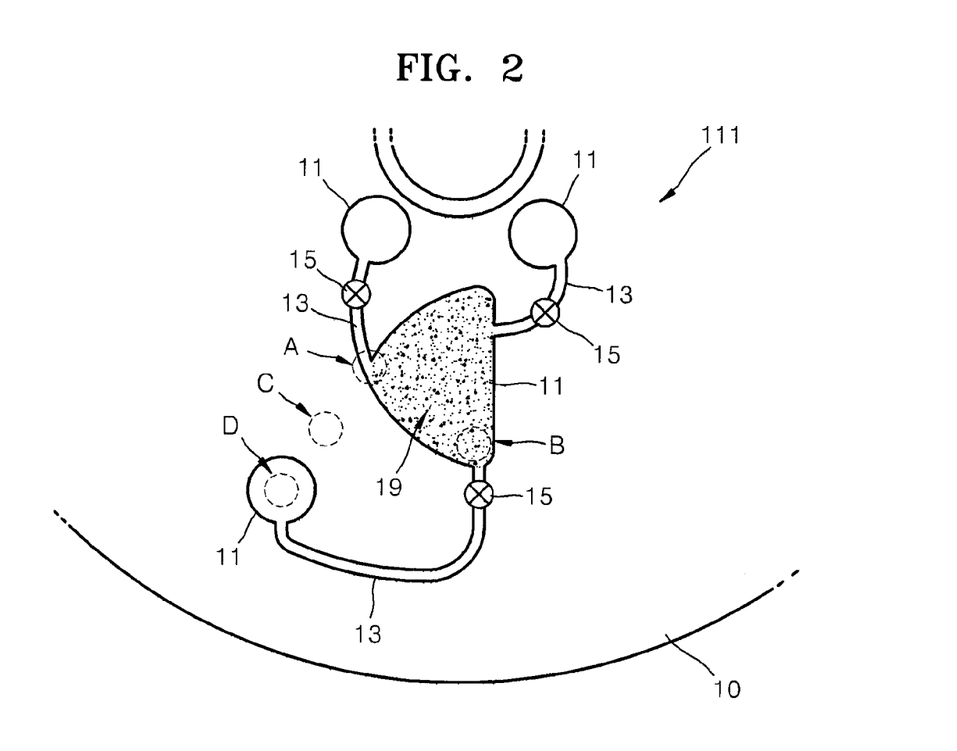
FIG. 2 is a plane view illustrating a first layer of the centrifugal micro fluidic system of FIG. 1, according to an exemplary embodiment of the present invention.

FIG. 2 is a plane view illustrating the first layer 10 of the centrifugal micro fluidic system of FIG. 1, according to an exemplary embodiment of the present invention. The micro fluidic structure 111 illustrated in FIG. 1 is only a non-limiting example of a micro fluidic structure that can be formed in the disk-shaped platform 100, and any type of micro-fluidic structure capable of moving a fluid by a centrifugal force can be applied to the micro fluidic system of the present exemplary embodiment. The micro fluidic system includes the micro fluidic structure 111 in the first layer 10 of the disk-shaped platform 100. The micro fluidic structure 111 includes the chambers 11, the channels 13 connecting the chambers 11, and valves 15 disposed on mid portions of the channels 13 for controlling flows of a fluid contained in the micro fluidic structure 111. The fluid contained in the micro fluidic structure 111 can be moved by a centrifugal force generated by rotation of the platform 100.

In the micro fluidic system according to the present exemplary embodiment, the micro fluidic structure 111 can be used to mix magnetic beads 19 with a fluid sample to perform a certain task, such as, separation of target bio-molecules. Then, in order to perform another task using the magnetic beads 19, it is necessary to control the position of the magnetic beads 19 in the micro fluidic structure 111, independently of the transfer of the fluid sample. For example, the fluid sample is discharged from the chamber 11 in which the fluid sample is mixed with the magnetic beads 19, while keeping the magnetic beads 19 collected at a corner of the chamber 11; a buffer solution is filled in the chamber 11; and the collected magnetic beads 19 are again dispersed to perform another task, such as a cleaning. In this case, it is necessary to control the magnetic beads 19 using means other than the centrifugal force. To control the position of the magnetic beads 19, it is necessary to selectively dispose a magnet outside the micro fluidic structure 111 at a variety of positions, for example, positions A, B, C, and D marked in FIG. 2.

Figure 3:
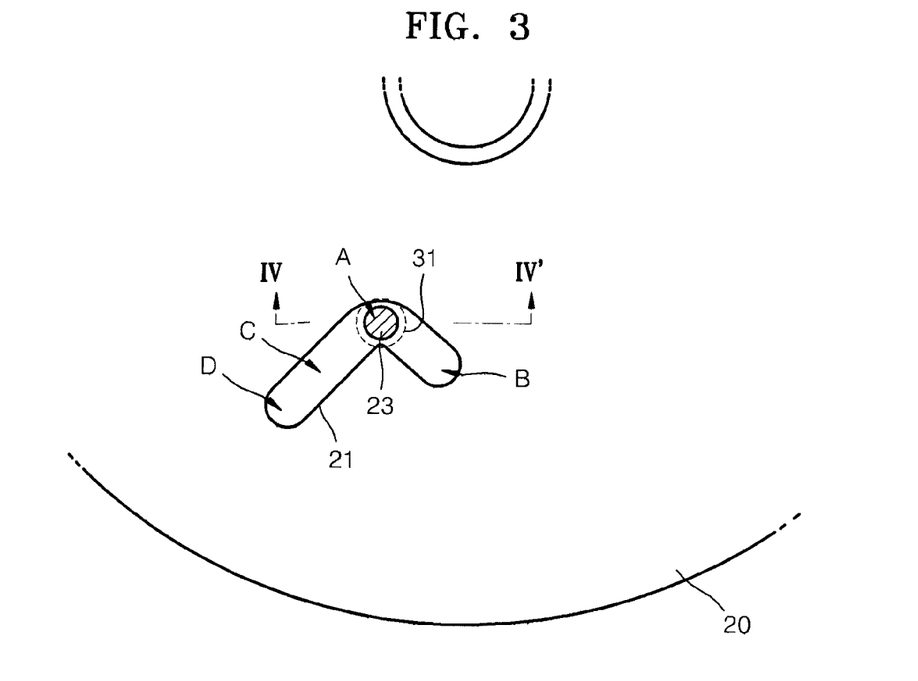
FIG. 3 is a plane view illustrating a second layer of the centrifugal micro fluidic system of FIG. 1, according to an exemplary embodiment of the present invention.

Since the first layer 10 of the platform 100 rotates, a magnet position control device is needed in order to dispose a magnet at a variety of positions such as the positions A, B, C and D while rotating with the first layer 10 in which the micro fluidic structure 111 is formed. FIG. 3 is a plane view illustrating the second layer 20 of the centrifugal micro fluidic system of FIG. 1, according to an exemplary embodiment of the present invention. The second layer 20 includes the guide rail 21. For example, the guide rail 21 may have an inverse V shape corresponding to the positions A, B, C, and D. The guide rail 21 can be formed by defining a trench or a channel in the second layer 20 of the disk-shaped platform 100. The first magnet 23 is disposed in the guide rail 21, and the movement of the first magnet 23 is guided along the guide rail 21. The guide rail 21 can have various shapes other than the inverse V shape shown in FIG. 3, such as an inverse U shape, a P-shape, an S-shape, and a 5-shape depending on positions at which the first magnet 23 is to be placed. That is, the guide rail 21 may have any shape as long as it can connect a variety of positions where the first magnet 23 needs to be placed, at different distances from a rotational axis of the second layer 20.

Meanwhile, a second magnet 31 may be disposed under the second layer 20 and permanently fixed to a preset position corresponding to a position of the first magnet 23 that is the closest to the rotational axis of the platform 100. Otherwise, the second magnet 31 may be fixed to the preset position at least temporarily while the platform 100 (refer to FIG. 1) rotates. When the guide rail 21 has an inverse V shape as shown in FIG. 3, it can be branched into two passages toward a distal direction from the rotational axis, starting from the closest position A to the rotational axis. In this case, the second magnet 31 may be fixedly disposed at a position corresponding to the closest position A to the rotational axis, at least while the platform 100 is rotating.

Figure 4:
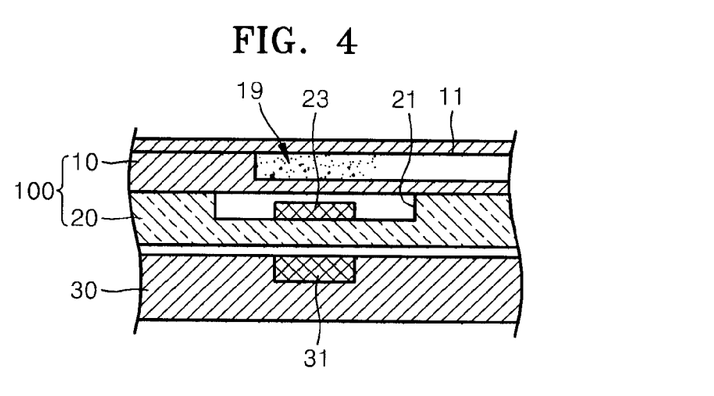
FIG. 4 is a sectional view taken along line IV-IV' of FIG. 1, according to an exemplary embodiment of the present invention.

FIG. 4 is a sectional view taken along line IV-IV' of FIG. 1, according to an exemplary embodiment of the present invention. FIG. 4 illustrates a vertical structure of the centrifugal micro fluidic system. The vertical structure includes the first layer 10 in which the micro fluidic structure 111 having the chambers 11 is formed, the second layer 20 having the guide rail 21 in which the first magnet 23 is disposed, and a base part 30 in which the second magnet 31 is disposed. The second magnet 31 and the first magnet 23 can be arranged with opposite poles facing each other to attract each other. Alternatively, the second magnet 31 and the first magnet 23 can be arranged with like poles facing each other to repel each other. In the latter case, the position of the second magnet 31 should be different from the position shown in FIG. 2. Also, the second magnet 31 may generate a magnetic field to such a degree that only the first magnet 23 is directly influenced by the magnetic field of the second magnet 31 and the magnetic beads 19 contained in the chamber 11 are not directly influenced by the magnetic field of the second magnet 31. Thus, only the first magnet 23 generates a magnetic force acting on the magnetic beads 19 so that the magnetic beads 19 can be gathered or moved by the magnetic force.

The first magnet 23 may be a permanent magnet. More specifically, the first magnet 23 can be a permanent magnet selected from the group consisting of a ceramics permanent magnet group including barium ferrite, strontium ferrite and the like, a rare-earth permanent magnet group including samarium-cobalt, neodium and the like, an alloy permanent magnet group including alnico (aluminum-nickel-cobalt) and the like, and a polymer-based magnet group including a rubber magnet and a plastic magnet. For miniaturization of the micro fluidic system, the first magnet 23 may have a small size and generate a large magnetic force. In the current exemplary embodiment, a neodium magnet is used as the first magnet 23. The second magnet 31 may be a permanent magnet or an electromagnet. Since the second magnet 31 is equipped in a fixed frame, it has a less limitation in size.

Figure 5A:
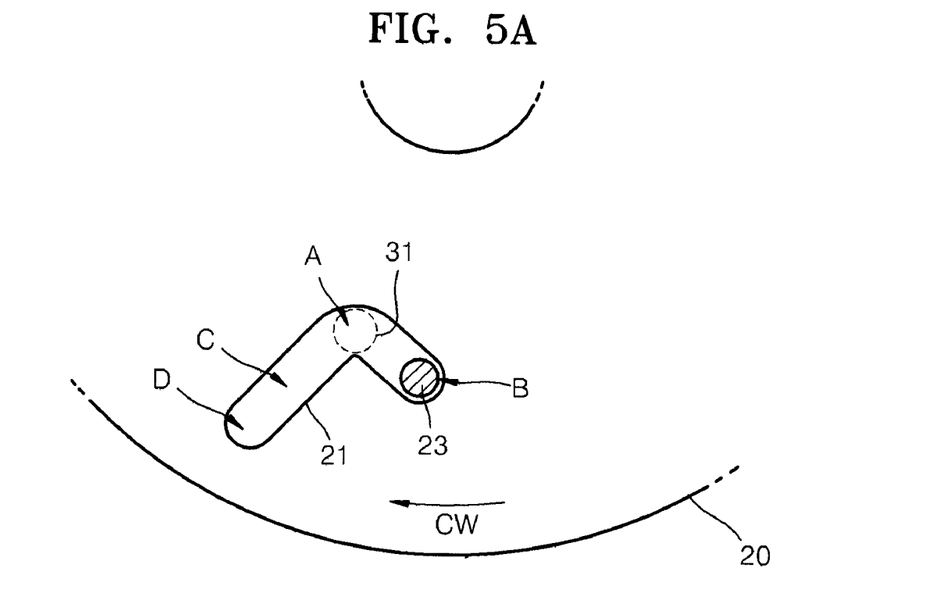
FIGS. 5A through 5C illustrate a variety of operation modes of a magnet position control device of the centrifugal micro fluidic system of FIG. 1, according to an exemplary embodiment of the present invention.
Figure 5B:
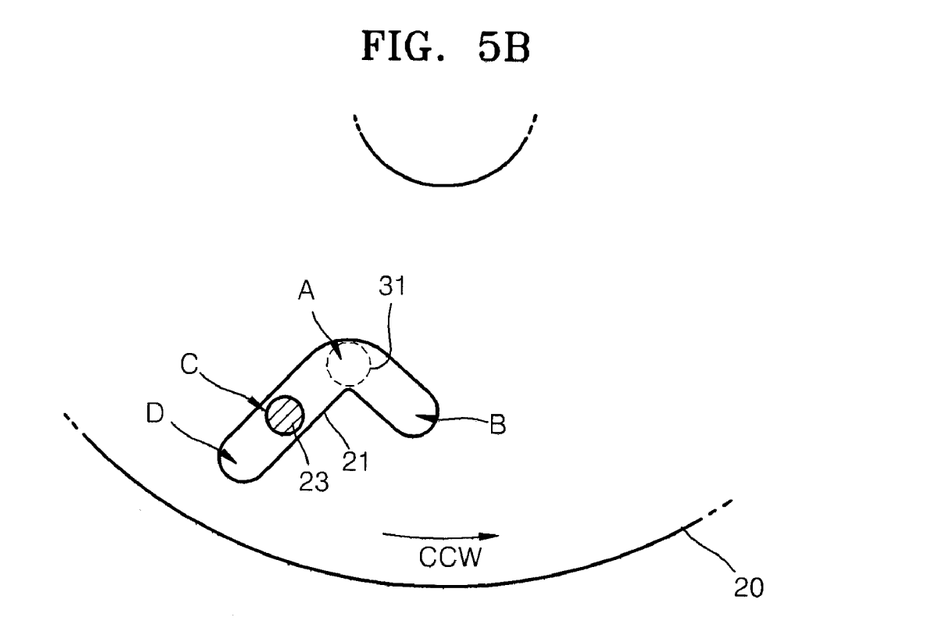
Figure 5C:
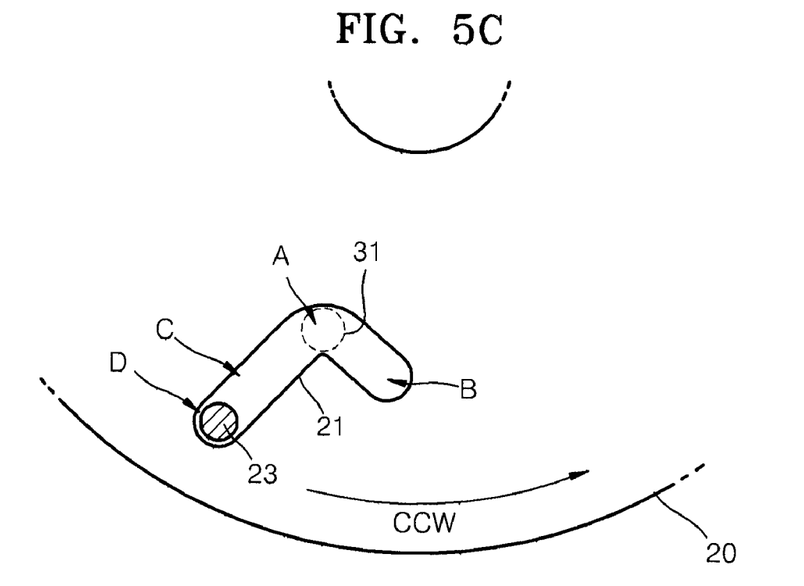

FIGS. 5A through 5C illustrate a variety of operation modes of the magnet position control device of the centrifugal micro fluidic system of FIG. 1, according to an exemplary embodiment of the present invention. FIG. 5A illustrates a mode when the platform 100 rotates clockwise (CW) at a rotational speed of 100 rpm. As aforementioned, the second magnet 31 having the fixed position is disposed corresponding to the position A closest to the rotational axis. When the platform 100 is accelerated clockwise, the first magnet 23 is biased to the right by an inertial force. As the rotational speed of the platform 100 increases, the first magnet 23 moves to the position B where an attractive force from the second magnet 31 is equilibrated with a centrifugal force. While the rotational speed of the platform 100 is kept constant, the first magnet 23 stays at the position B, and as the rotational speed decreases, the first magnet 23 returns to the position A. At this time, in the micro fluidic structure 111 of the first layer 10 of the platform 100, the magnetic beads 19 are collected at the position B marked in FIG. 2. In the above, the rotational speed of 100 rpm is only one example, and it can vary with the magnetic flux density of the first and second magnets 23 and 31 and a distance between the positions A and B. The above fact is equally valid in the following modes.

FIG. 5B illustrates a mode when the platform 100 rotates counterclockwise (CCW) at a rotational speed of 150 rpm. When the platform 100 is accelerated counterclockwise, the first magnet 23 is biased to the left by an inertial force. As the rotational speed of the platform 100 increases, the first magnet 23 moves to the position C where an attractive force from the second magnet 31 is equilibrated with a centrifugal force. While the rotational speed of the platform 100 is kept constant, the first magnet 23 stays at the position C, and as the rotational speed decreases, the first magnet 23 returns to the position A. At this time, the magnetic beads 19 contained in the chamber 11 of the first layer 10 formed above the second layer 20 are kept in a dispersed state without being influenced by the first magnet 23.

FIG. 5C illustrates a mode when the platform 100 rotates counterclockwise (CCW) at a rotational speed of 1000 rpm. Likewise, when the platform 100 is accelerated counterclockwise, the first magnet 23 is biased toward the left of the drawing due to an inertial force. As the rotational speed of the platform 100 increases, the first magnet 23 moves to a distal position away from the second magnet 31. As the rotational speed of the second layer 20 increases, the centrifugal force increases so that the first magnet 23 moves to a distal position further away from the rotational axis, and as the rotational speed decreases, the first magnet 23 returns to the original position A. Then, since an attractive force between the first magnet 23 and the second magnet 31 decreases as a distance therebetween increases, at a rotational speed higher than a predetermined level, the first magnet 23 moves to and stays at the position D where the guide rail 21 ends. At this time, in the micro fluidic structure 111 of the first layer 10 formed above the second layer 20, the magnetic beads 19 are collected in the chamber 11 corresponding to the position D.

Figure 6:
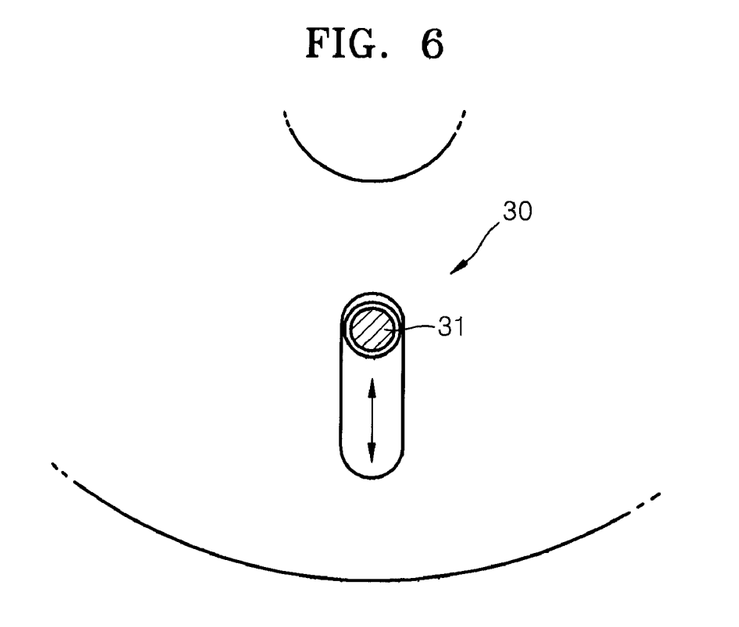
FIG. 6 is a plane view illustrating a base part of the centrifugal micro fluidic system of FIG. 1, according to an exemplary embodiment of the present invention.

FIG. 6 is a plane view illustrating the base part 30 of the micro fluidic system according to an exemplary embodiment of the present invention. In FIG. 6, the base part 30 is a part of the fixed frame in the micro fluidic system of the present invention, and the platform 100 is rotatably disposed on the base part 30. The aforementioned construction corresponds to an example where the second layer 20 is disposed below the first layer 10, but it is different from an example where the second layer 20 is disposed on the first layer 10.

The second magnet 31 which can be temporarily fixed on the base part 30 is fixed at least while the second layer is rotating. However, like in the mode shown in FIG. 5C, after the first magnet 23 gets out of an attractive force range of the second magnet 31 fixed at one position, a second magnet moving unit (not shown) can be used to move the second magnet 31 in a radial direction of the platform 100 so as to place the first magnet 23 in the attractive force range of the second magnet 31. The second magnet moving unit can be used only if it can be installed on the base part 30, which is a fixed frame to move the second magnet 31. Accordingly, while a detailed description of the second magnet moving unit is not given in the present specification, the second magnet moving unit can be easily implemented by one of ordinary skill in the related art.

Figure 7:
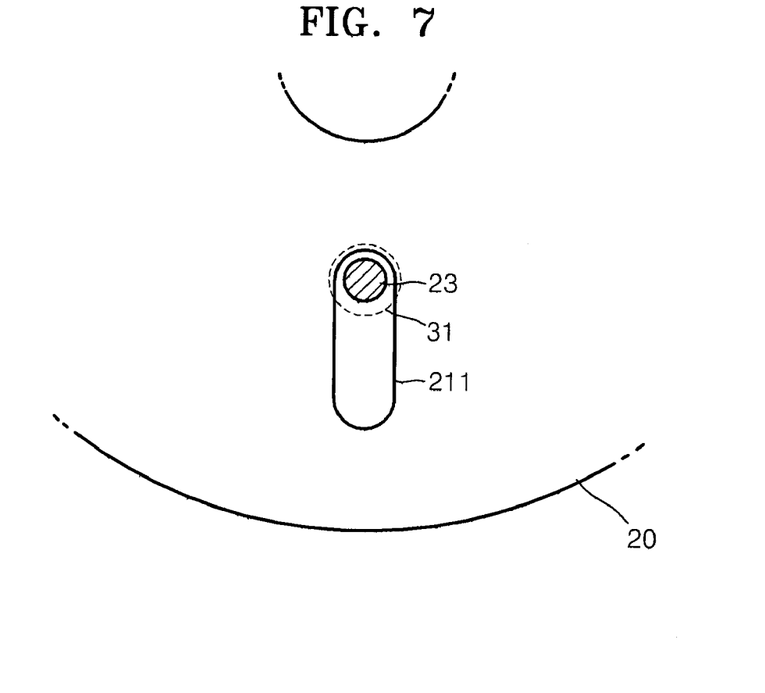
FIG. 7 is a plane view illustrating another version of the magnet position control device of the centrifugal micro fluidic system of FIG. 1, according to an exemplary embodiment of the present invention.

FIG. 7 is a plane view illustrating a modification version of the magnet position control device of the centrifugal micro fluidic system of FIG. 1, according to an exemplary embodiment of the present invention. As aforementioned, a guide rail 211 is a path connecting the positions where a first magnet 23 is temporarily disposed. The guide rail 211 may have various shapes or a simple straight line shape as shown in FIG. 7.

Figure 8:
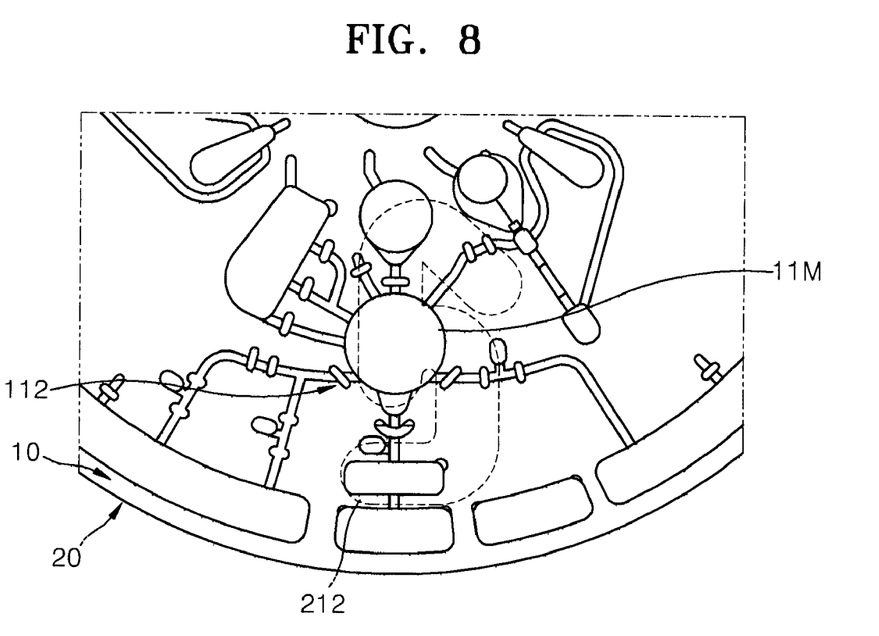
FIGS. 8 through 10 illustrate centrifugal micro fluidic systems according to other exemplary embodiments of the present invention.
Figure 9:
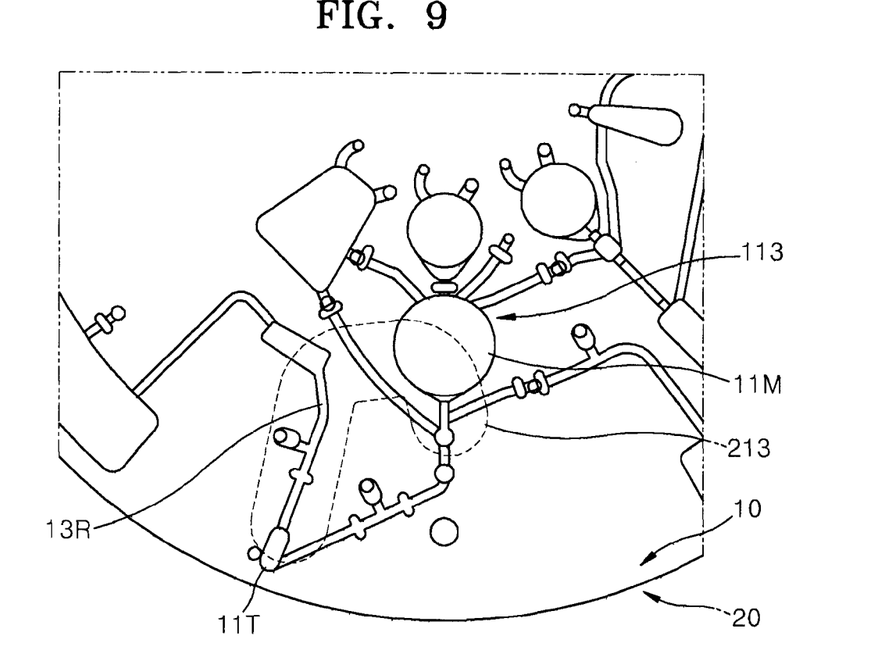
Figure 10:
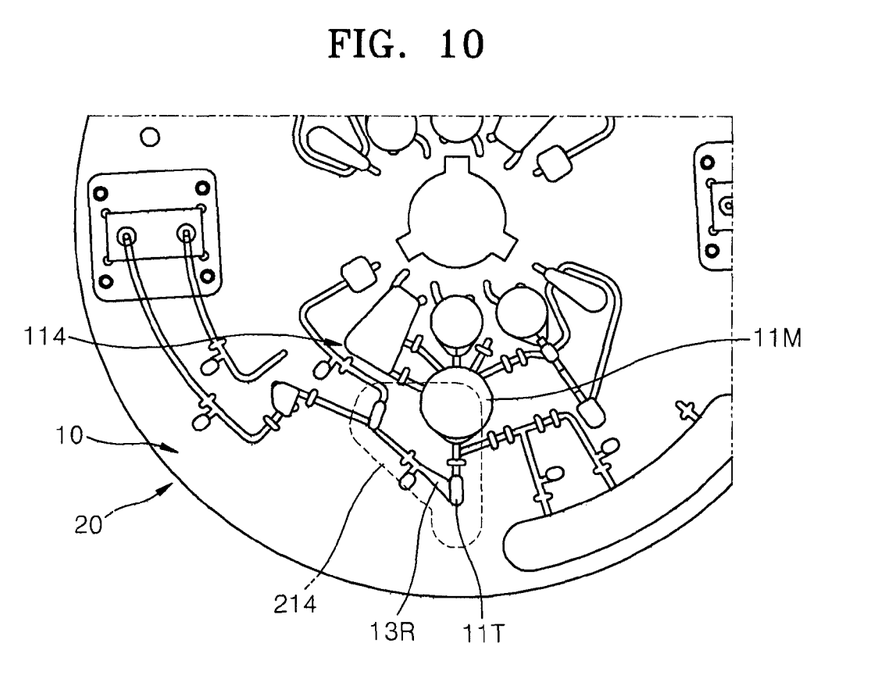

FIGS. 8 through 10 illustrate centrifugal micro fluidic systems according to other exemplary embodiments of the present invention. In the exemplary embodiments of FIGS. 8 through 10, suitably configured micro fluidic structures 112, 113, and 114 are formed in first layers 10, respectively. Guide rails 212, 213, and 214 having different shapes are formed in second layers 20, respectively. The respective guide rails 212, 213, and 214 provide paths to collect magnetic beads in the micro fluidic structures 112, 113, and 114, independently of a movement of a fluid by a centrifugal force. Each of these paths connects a plurality of positions having different distances from a rotational axis. Although not shown in FIGS. 8 through 10, a first magnet (not shown) is mounted on each of the guide rails 212, 213, and 214. The position of the first magnet (not shown) is controlled by a combination of a centrifugal force caused by the rotation of the first and second layers 10 and 20 and an interaction between the first magnet and a second magnet (not shown) disposed in a base part (not shown).

In the aforementioned exemplary embodiments, the first layer 10 and the second layer 20 can be attached in an up and down direction by bonding two substrates as shown in FIG. 4. However, it is not necessary to form the first and second layers 10 and 20 using separate substrates. For example, the first and second layers 10 and 20 can be formed using a single substrate, the guide rail 212, 213, or 214 can be formed in a trench shape in a bottom surface of the substrate opposite to a surface of the substrate where the micro fluidic structure 112, 113, or 114 is formed. In this case, a bottom cover (not shown) can be further provided such that the first magnet (not shown) may not fall down from the guide rail 212, 213, or 214.

The micro fluidic structures 112, 113, and 114 illustrated in FIGS. 8 through 10 include mixing chambers 11M, respectively. Each of the guide rails 212, 213, and 214 corresponding to the micro fluidic structures 112, 113, and 114 may include a section running from a position corresponding to an outlet of the mixing chamber 11M disposed away from the center of the mixing chamber 11M to a position corresponding to the center of the mixing chamber 11M. Thus, after magnetic beads are collected toward the inside of the outlet by a centrifugal force, the magnetic beads can be moved back to the center of the mixing chamber 11M.

Meanwhile, each of the micro fluidic structures 113 and 114 illustrated in FIGS. 9 and 10 may include a trapping chamber 11T for collecting magnetic beads, and a reverse channel 13R connected to the trapping chamber 11T. The reverse channel 13R extends from the trapping chamber 11T in an opposite direction to that of a centrifugal force. Each of the guide rails 213 and 214 corresponding to the micro fluidic structures 113 and 114 may include a section running along the reverse channel 13R. In this case, the first magnet (not shown) can be moved in the guide rail 213 or 214 from a position corresponding to the trapping chamber 11T along the section running along the reverse channel 13R so as to move the magnetic beads (not shown) in a direction opposite to that of a centrifugal force.

Figure 11A:
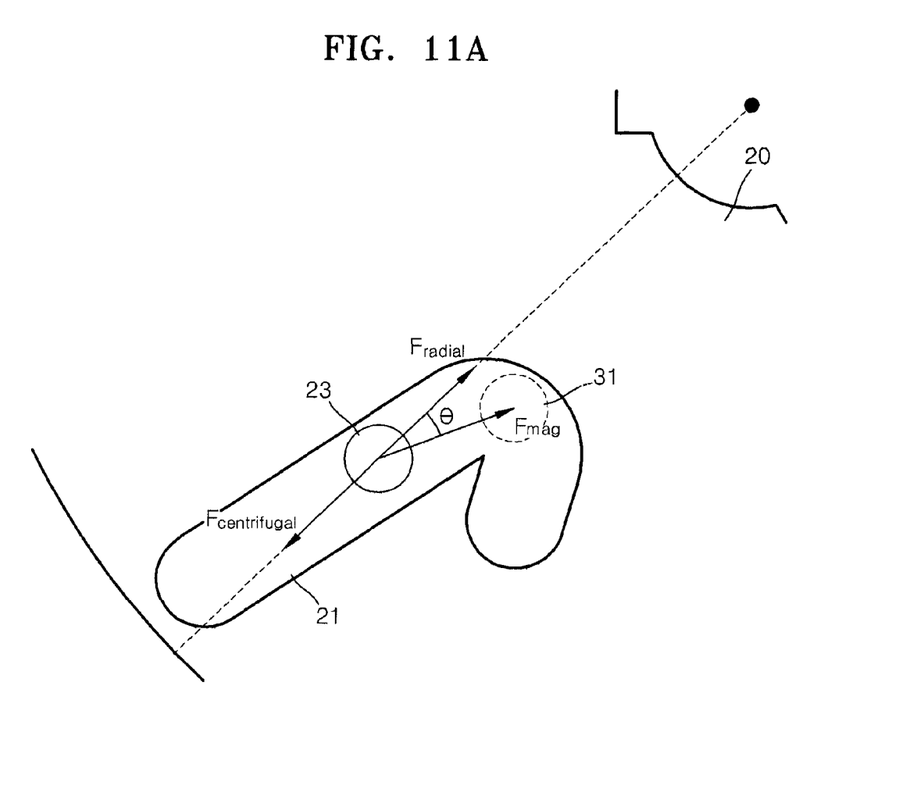
FIGS. 11A and 11B are free body diagrams illustrating forces acting on a first magnet in the centrifugal micro fluidic system of FIG. 1.
Figure 11B:
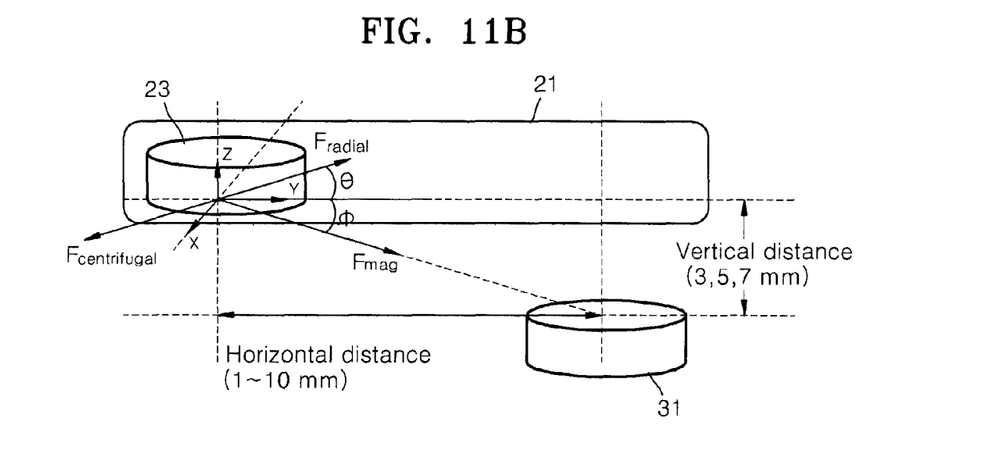

FIGS. 11A and 11B are free body diagrams illustrating forces acting on the first magnet 23 in the centrifugal micro fluidic system of FIG. 1. When the guide rail 21 has the same shape as that shown in FIGS. 11A and 11B, the forces acting on the first magnet 23 are as follows.

First, a centrifugal force acts on the first magnet 23, $F_{cent} = mr\omega^2$, where m is a weight of the first magnet 23, r is a distance from a rotational center, and $\omega$ is an angular velocity. The centrifugal force$_{cent}$ is parallel with a radial component $F_{radial}$ of a magnetic force of the second magnet 31.

Here, $|F_{radial}| = |F_{mag}| \times \cos(\theta) \times \cos(\phi)$.

Meanwhile, $F_{mag} = \nabla U_{mag}$, and an instant energy density ($U_{mag}$) of a magnetic field is given by an equation $U_{mag}=\frac{1}{2}B \cdot H$. Nd—Fe—B magnets employed as the first and second magnets 23 and 31 in the present exemplary embodiment have the following physical properties: μr (relative permeability) is 1.04457301671; σ (conductivity) is $6.25*10^5$ [siemens/meter]; Hc (magnetic coercivity) is $-8.38*10^5$ [Ampere/meter]; Br (magnetic retentivity) is 1.1 [Tesla]; and M (magnetization) is 875352.188006 [Ampere/meter].

Figure 12:
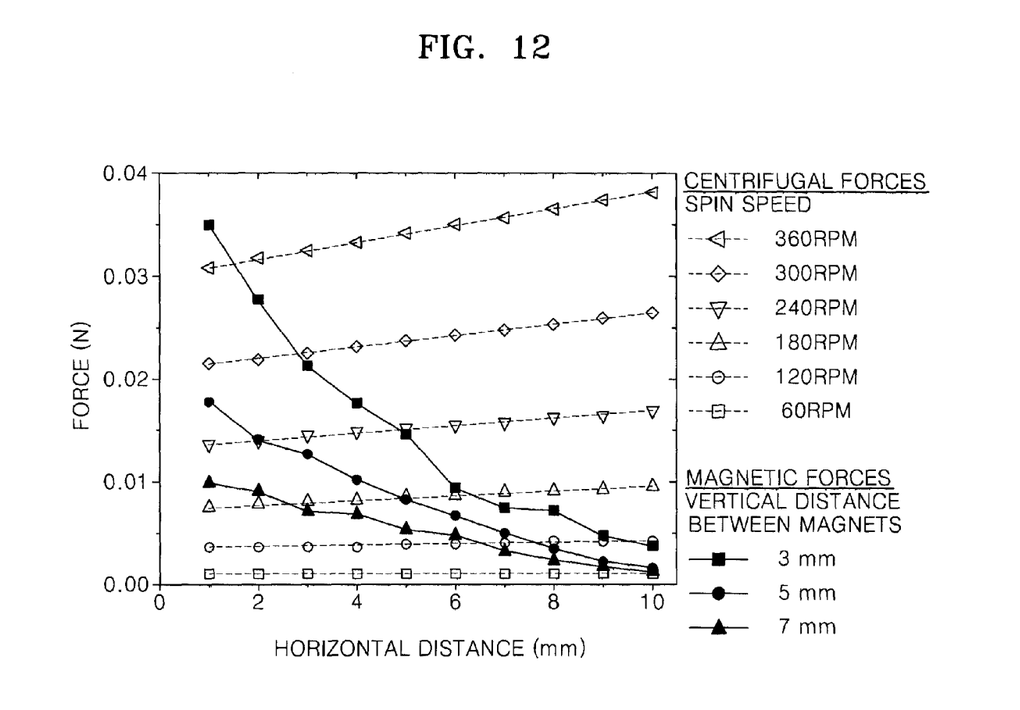
FIG. 12 is a graph illustrating the relationships between a horizontal distance and magnetic and centrifugal forces in FIG. 11B.

FIG. 12 is a graph illustrating magnetic and centrifugal forces with respect to a horizontal distance indicated in FIG. 11B. When the first and second magnets 23 and 31 have the above physical properties, a horizontal distance between the first and second magnets 23 and 31 in an equilibrium state is calculated as shown in FIG. 12 according to a rotational velocity of the platform 100 and a vertical distance between the first and second magnets 23 and 31.

For example, when the rotational velocity is 300 rpm and the vertical distance is 3 mm, a magnetic force is higher than a centrifugal force until the horizontal distance reaches 3 mm. When the horizontal distance exceeds 3 mm, the centrifugal force is larger than the magnetic force. Although not shown in the graph, when the rotational velocity exceeds 420 rpm, the centrifugal force is always larger than the magnetic force. At this time, the first magnet 23 gets out of a magnetic range of the second magnet 31 and moves to the most distal position in the guide rail 21 from the rotational axis.

As described above, in a disk-shaped micro fluidic system of the present invention, the position of a magnet is controlled two-dimensionally using a centrifugal force caused by a rotational movement. Therefore, the position of magnetic beads can be controlled independently of a movement of a fluid sample caused by the centrifugal force.

Also, since the position of the magnet is controlled while rotating the magnet together with the disk-shaped platform having the micro fluidic structure, the present invention is advantageous in the miniaturization and simplification of the micro fluidic system operating using magnetic beads and capable of controlling the position of magnetic beads.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A centrifugal micro fluidic system comprising:
   a rotatable platform which includes a first layer and a second layer disposed adjacent to a top or bottom side of the first layer;
   a micro fluidic structure which is disposed in the first layer of the platform and includes a chamber which is capable of accommodating a fluid, a channel through which the fluid can flow, and a valve which controls the flow of the fluid;
   magnetic beads which include functional groups on surfaces thereof so as to capture a target material from a sample, the magnetic beads carrying the target material while moving in the micro fluidic structure;
   a guide rail which is disposed in the second layer of the platform, the guide rail connecting a plurality of positions located outside of and adjacent to a path in the micro-fluidic structure through which the magnetic beads move, the plurality of positions being spaced away from a rotational center of the platform at different distances;
   a first magnet which is movably disposed in the guide rail and generates a magnetic force for moving the magnetic beads;
   a second magnet which is disposed outside the platform at a location closer to the second layer than the first layer; and
   a driving unit which rotates the platform.

2. The centrifugal micro fluidic system of claim 1, wherein the platform is formed of a material that does not have a magnetic property and does not block a magnetic force.

3. The centrifugal micro fluidic system of claim 1, wherein the platform has a disk shape.

4. The centrifugal micro fluidic system of claim 1, wherein the first magnet and the second magnet are disposed such that an attraction force is generated therebetween.

5. The centrifugal micro fluidic system of claim 1, wherein the second magnet has a fixed position at least while the platform rotates.

6. The centrifugal micro fluidic system of claim 1, wherein the guide rail comprises a section which branches into two branches away from the rotational center of the platform.

7. The centrifugal micro fluidic system of claim 1, wherein the first magnet is a permanent magnet and the second magnet is a permanent magnet or electromagnet.

8. The centrifugal micro fluidic system of claim 7, wherein the first magnet is a magnet selected from the group consisting of a ceramic permanent magnet, a rare-earth permanent magnet, an alnico permanent magnet, and a polymer permanent magnet.

9. The centrifugal micro fluidic system of claim 1, wherein the functional groups on the surfaces of the magnetic beads are antigens, antibodies, or metal oxides having an affinity to the target material.

10. The centrifugal micro fluidic system of claim 9, wherein the metal oxides are metal oxides selected from the group consisting of $Al_2O_3$, $TiO_2$, $Ta_2O_3$, $Fe_2O_3$, $Fe_3O_4$, and $HfO_2$.

11. The centrifugal micro fluidic system of claim 1, wherein the magnetic beads comprise at least one ferromagnetic material selected from the group consisting of iron (Fe), nickel (Ni), chromium (Cr), and an oxide.

12. The centrifugal micro fluidic system of claim 1, wherein the micro fluidic structure further includes a trapping chamber which collects the magnetic beads, and a reverse channel which is connected to the trapping chamber and extends from the trapping chamber in a direction opposite to that of a centrifugal force, and
   the guide rail includes a section running along the reverse channel,
   wherein the magnetic beads collected in the trapping chamber are moved in the direction opposite to that of the centrifugal force by moving the first magnet in the guide rail from a position corresponding to the trapping chamber along the section of the guide rail.

13. The centrifugal micro fluidic system of claim 1, wherein the micro fluidic structure further includes a mixing chamber in which the magnetic beads are mixed with the sample, the mixing chamber including an outlet formed at a position away from the rotational center of the platform, and
   the guide rail includes a section running from a position corresponding to the outlet of the mixing chamber to a position corresponding to a portion of the mixing chamber closer to the rotation center of the platform than the outlet of mixing chamber,
   wherein after the magnetic beads are collected to an inside of the outlet of the mixing chamber by a centrifugal force, the magnetic beads are moved back to the portion of the mixing chamber closer to the rotation center of the platform than the outlet of the mixing chamber.

14. A method of operating the centrifugal micro fluidic system of claim 1, the method comprising adjusting a rotational speed of the platform according to a horizontal distance between the second magnet and a position in the guide rail where the first magnet is to be placed, so as to balance a centrifugal force acting on the first magnet with a magnetic force acting between the first and second magnets.

15. A method of operating the centrifugal micro fluidic system of claim 6, the method comprising:
selecting a rotational direction of the platform depending on a direction of one of the two branches where the first magnet is moved; and
adjusting a rotational speed of the platform according to a horizontal distance between the second magnet and a position in the guide rail where the first magnet is to be placed, so as to balance a centrifugal force acting on the first magnet with a magnetic force acting between the first and second magnets.

16. A centrifugal magnetic position control device comprising:
a rotatable platform which includes a first layer and a second layer disposed adjacent to a top or bottom side of the first layer;
a micro fluidic structure which is disposed in the first layer of the platform and which includes a chamber which is capable of accommodating a fluid, a channel through which the fluid can flow, and a valve which controls the flow of the fluid;
a guide rail which is disposed in the second layer of the platform and which connects a plurality of positions located outside of and adjacent to a path in the micro fluidic structure, the plurality of positions being spaced away from a rotational center of the platform at different distances;
a first magnet which is movably disposed in the guide rail;
a second magnet which is disposed outside the platform and generates a magnetic force for moving the first magnet; and
a driving unit which rotates the platform.

17. The centrifugal magnetic position control device of claim 16, wherein the platform is formed of a material which does not have a magnetic property and does not block a magnetic force.

18. The centrifugal magnetic position control device of claim 16, wherein the platform has a disk shape.

19. The centrifugal magnetic position control device of claim 16, wherein the first magnet and the second magnet are disposed such that an attraction force is generated therebetween.

20. The centrifugal magnetic position control device of claim 16, wherein the second magnet has a fixed position at least while the platform rotates.

21. The centrifugal magnetic position control device of claim 16, wherein the guide rail comprises a section which branches into two branches away from the rotational center of the platform.

22. The centrifugal magnetic position control device of claim 16, wherein the first magnet is a permanent magnet and the second magnet is a permanent magnet or electromagnet.

23. The centrifugal magnetic position control device of claim 22, wherein the first magnet is a magnet selected from the group consisting of a ceramic permanent magnet, a rare-earth permanent magnet, an alnico permanent magnet, and a polymer permanent magnet.

* * * * *